United States Patent
Rezach et al.

(10) Patent No.: US 10,028,770 B2
(45) Date of Patent: Jul. 24, 2018

(54) SPINAL IMPLANT SYSTEM AND METHODS OF USE

(71) Applicant: Warsaw Orthopedic, Inc., Warsaw, IN (US)

(72) Inventors: William Alan Rezach, Atoka, TN (US); Jason May, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 14/518,760

(22) Filed: Oct. 20, 2014

(65) Prior Publication Data
US 2016/0106473 A1    Apr. 21, 2016

(51) Int. Cl.
*A61B 17/70* (2006.01)
(52) U.S. Cl.
CPC ...... *A61B 17/7035* (2013.01); *A61B 17/7032* (2013.01)
(58) Field of Classification Search
CPC ............ A61B 17/7034; A61B 17/7035; A61B 17/7037; A61B 17/7038
See application file for complete search history.

(56) References Cited

U.S. PATENT DOCUMENTS

| | | | | |
|---|---|---|---|---|
| 5,885,286 | A * | 3/1999 | Sherman | A61B 17/7037 606/266 |
| 6,280,442 | B1 * | 8/2001 | Barker | A61B 17/7037 606/256 |
| 6,485,491 | B1 * | 11/2002 | Farris | A61B 17/7002 606/250 |
| 6,716,214 | B1 * | 4/2004 | Jackson | A61B 17/7032 606/266 |
| 9,084,634 | B1 * | 7/2015 | Lab | A61B 17/7038 |
| 2008/0161859 | A1 * | 7/2008 | Nilsson | A61B 17/7032 606/266 |
| 2009/0248075 | A1 * | 10/2009 | Ogilvie | A61B 17/7005 606/246 |
| 2010/0036433 | A1 * | 2/2010 | Jackson | A61B 17/7037 606/302 |
| 2012/0041490 | A1 * | 2/2012 | Jacob | A61B 17/7032 606/264 |

* cited by examiner

*Primary Examiner* — Ellen C Hammond

(57) ABSTRACT

A spinal implant system comprises a plurality of alternate first members. Each of the first members includes an inner surface defining an implant cavity. A second member is configured to penetrate tissue and includes a mating element engageable with a first member such that the second member is interchangeable with the plurality of first members. A first member is selected for connection with the second member to comprise a bone fastener having a selected movement. Fasteners, instruments and methods are disclosed.

18 Claims, 6 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including a bone fastener.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a spinal implant system is provided. The spinal implant system comprises a plurality of alternate first members. Each of the first members includes an inner surface defining an implant cavity. A second member is configured to penetrate tissue and includes a mating element engageable with a first member such that the second member is interchangeable with the plurality of first members. A first member is selected for connection with the second member to comprise a bone fastener having a selected movement. In some embodiments, fasteners, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
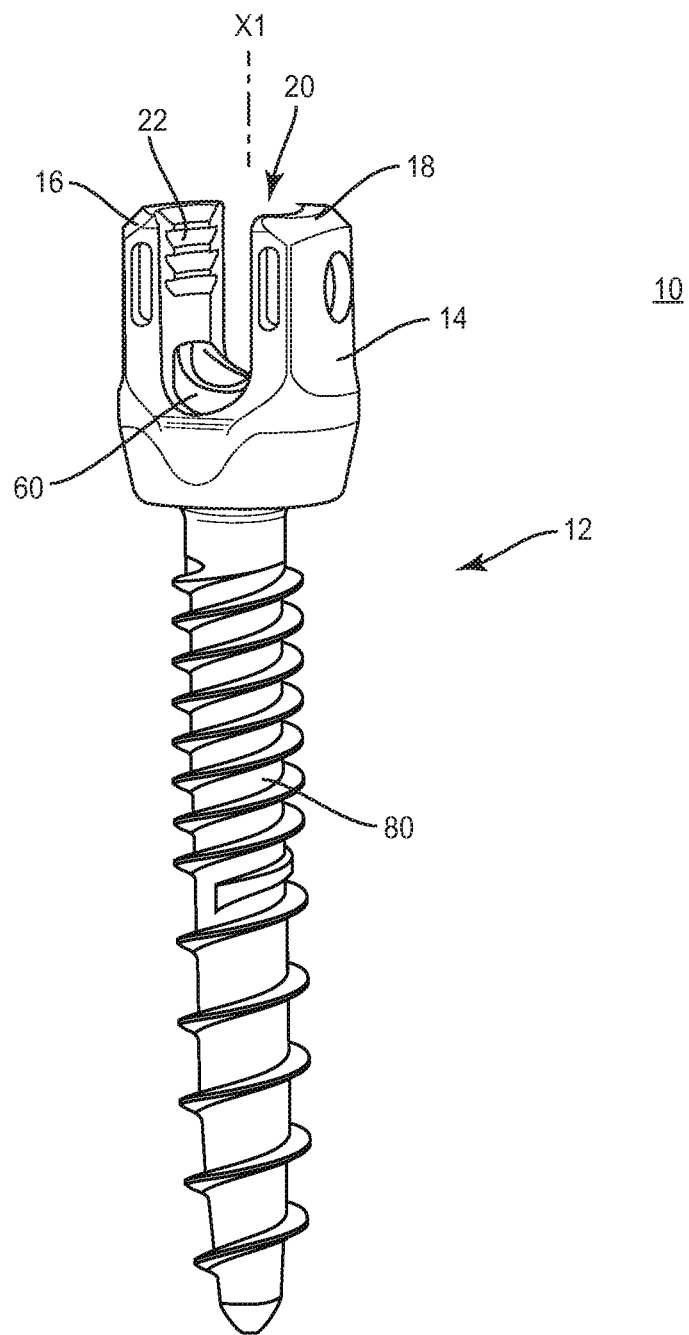
FIG. 1 is a perspective view of components of one embodiment of a spinal implant system in accordance with the principles of the present disclosure.
Figure 2:
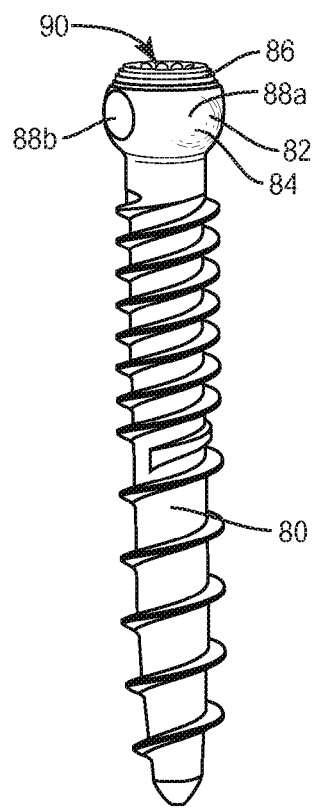
FIG. 2 is a perspective view of a component of the system shown in FIG. 1.
Figure 3:
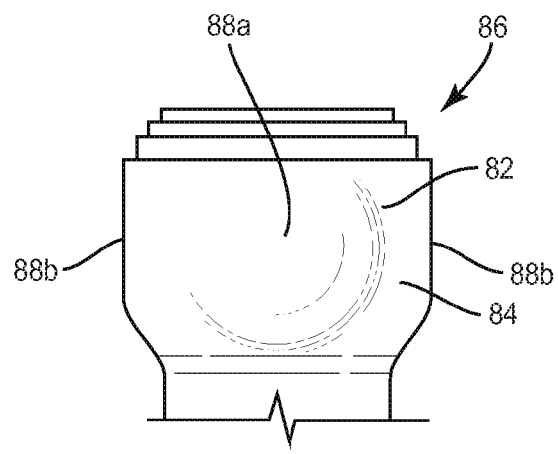
FIG. 3 is a break away view of the component shown in FIG. 2.

The exemplary embodiments of a surgical system and related methods of use disclosed are discussed in terms of medical devices for the treatment of musculoskeletal disorders and more particularly, in terms of a spinal implant system including a bone fastener. In one embodiment, the spinal implant system includes an implant comprising a bone fastener, such as, for example, a universal pedicle bone screw.

In some embodiments, the spinal implant system comprises a modular system including an array of members, such as, for example, receivers that can be selectively coupled to members, such as, for example, bone screw shafts. In some embodiments, the spinal implant system provides fewer bone screw options while providing multi-axial screw (MAS) functionality and/or uni-axial screw (UAS) functionality.

In one embodiment, the spinal implant system comprises a bone fastener having a universal screw design that includes one or more flats and/or a keyed geometry to facilitate UAS functionality. In some embodiments, the spinal implant system includes a bone fastener having a band, such as, for example, a ring that has a gap smaller than its height and/or width. In some embodiments, this configuration maintains strength performance of the spinal implant system. In some embodiments, the spinal implant system is employed with a method of selectively mating members, such as, for example, heads and shafts, of the spinal implant system to achieve MAS functionality and/or UAS functionality from the same bone fastener depending on the selected head being placed onto the shaft.

In some embodiments, the spinal implant system includes a bone fastener having a screw shank. In some embodiments, the screw shank includes a mating element, such as, for example, flats on an outside surface thereof. In some embodiments, the bone fastener includes a ring disposed with a receiver connected with the screw shank. In some embodiments, the ring has a minimal gap to increase a retaining strength of the screw shank. In some embodiments, the ring has a gap, such as, for example, a slot having a slot thickness less than the height or width of the ring.

In some embodiments, the method includes the step of inserting the ring with the head. In some embodiments, the method includes the step of assembling a head with a shaft to achieve MAS functionality. In some embodiments, the method includes the step of assembling a head with a shaft to achieve MAS functionality such that the flats are not keyed to the head and the shaft is pivotable in a plurality of planes relative to an axis of the head. In some embodiments, the method includes the step of assembling a head with a shaft to achieve UAS functionality. In some embodiments, the method includes the step of assembling a head with a shaft to achieve UAS functionality such that the flats are keyed to the head and the shaft is pivotable in only one plane relative to an axis of the head. In some embodiments, the head defines a keyway for disposal of a head of the shaft. In some embodiments, the keyway is disposable in alternate orientations, such as, for example, sagittal or coronal.

In some embodiments, the spinal implant system includes a bone fastener that includes a shaft having at least one flat for keying into a receiver. In some embodiments, the bone fastener includes a ring having a cylindrical shape. In some embodiments, the method includes the step of assembling a bone fastener by employing a flexible wire insertion technique with the ring. In some embodiments, the method includes the step of inserting the ring into the head and through a hole of the head and deforming the ring into a C type of arrangement. In some embodiments, the method includes the step of attaching modular heads that provide different degrees of freedom to the same bone screw shaft depending on what head is placed onto the bone screw shaft. In some embodiments, the spinal implant system comprises a modular kit that includes a universal screw shank and modular receiver heads that can interface differently, for example, in a multi-axial, uni-axial and/or fixed configuration.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a spinal implant system 10 including a plurality of alternate bone fastener configurations, such as, for example, a plurality of bone screw configurations 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

In some embodiments, spinal implant system 10 comprises a spinal implant kit, which includes a plurality of members, such as, for example, implant receivers 14. Receiver 14 is configured for selection from the plurality of receivers such that receiver 14 is connectable with an interchangeable member, such as, for example, a shaft 80. In some embodiments, receiver 14 is configured for selection from the plurality of receivers such that receiver 14 is connectable with a compatible shaft 80.

An interchangeable mating element, such as, for example, a head 82 of shaft 80 is interchangeable with a mating element, as described herein, of each of the plurality of receivers 14 to form a selected bone screw 12 having a selected movement of its components parts and/or movement relative to tissue. In some embodiments, the selected movement includes rotation and/or pivotal movement of shaft 80 relative to receiver 14 about one or a plurality of axes. In some embodiments, the selected movement includes rotation and/or pivotal movement of shaft 80 relative to receiver 14 through one or a plurality of planes. In some embodiments, shaft 80 is connected to a selected receiver 14 to comprise a multi-axial fastener. In some embodiments, shaft 80 is connected to a selected receiver 14 to comprise a uni-axial fastener. In some embodiments, spinal implant system 10 comprises a spinal implant kit, which includes receivers 14 and alternate receivers, such as those described herein.

Figure 4:
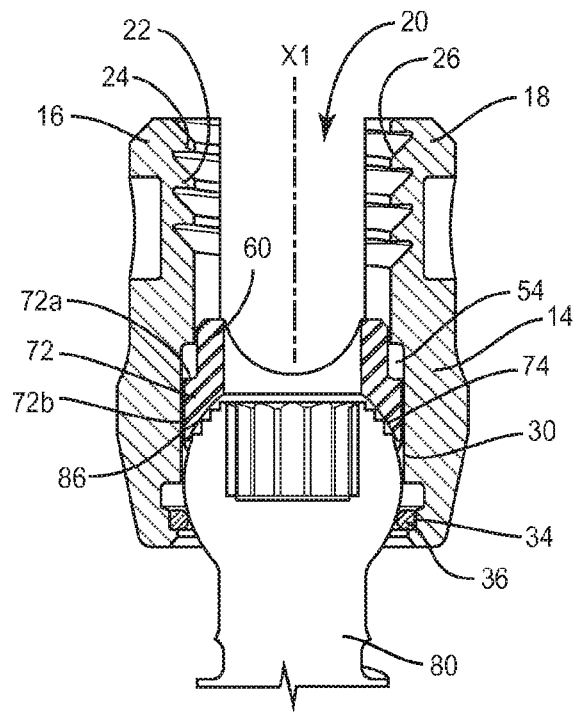
FIG. 4 is a break away, cross section view of the components shown in FIG. 1.

Each receiver 14 extends along and defines an axis X1. Each receiver 14 includes a pair of spaced apart arms 16, 18 that define an implant cavity 20 therebetween configured for disposal of a component of a spinal construct, such as, for example, a spinal rod (not shown). Arms 16, 18 each extend parallel to axis X1, as shown in FIG. 4. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone screw 12. In some embodiments, arms 16, 18 are connected at proximal and distal ends thereof such that receiver 14 defines a closed spinal rod slot.

Cavity 20 is substantially U-shaped. In some embodiments, all or only a portion of cavity 20 may have alternate cross section configurations, such as, for example, closed, V-shaped, W-shaped, oval, oblong triangular, square, polygonal, irregular, uniform, non-uniform, offset, staggered, and/or tapered. Each receiver 14 includes an inner surface 22. A portion of surface 22 includes a thread form 24 located adjacent arm 16 and a thread form 26 located adjacent arm 18, as shown in FIG. 4. Thread forms 24, 26 are each configured for engagement with a coupling member, such as, for example, a setscrew (not shown), to retain a spinal construct, such as, for example, a spinal rod (not shown) within cavity 20. In some embodiments, surface 22 may be disposed with the coupling member in alternate fixation configurations, such as, for example, friction fit, pressure fit, locking protrusion/recess, locking keyway and/or adhesive. In some embodiments, all or only a portion of surface 22 may have alternate surface configurations to enhance engagement with the spinal rod and/or the setscrew such as, for example, rough, arcuate, undulating, mesh, porous, semi-porous, dimpled and/or textured.

Figure 5:
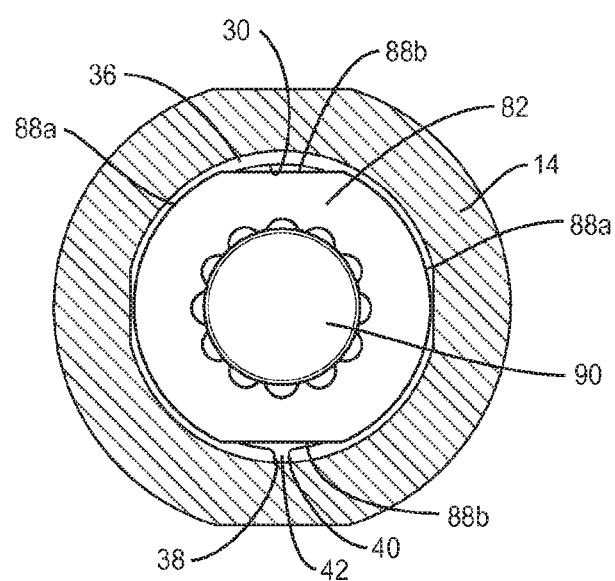
FIG. 5 is a cross section view of the components shown in FIG. 1.

A portion of surface 22 of each receiver 14 defines a particularly configured mating element, such as, for example, an engagement surface 30 configured to interface in a selective mating engagement with head 82 of shaft 80, as shown in FIG. 5. In one embodiment, as shown in FIGS. 1-7, head 82 is slidably engageable with surface 30 and movable relative thereto such that shaft 80 is rotatable along a plurality of axes relative to receiver 14 including rotation about axis X1. Interchangeable shaft 80 is connected with a selected receiver 14 from the kit of receivers 14 to form a multi-axial bone screw 12. In some embodiments, receiver 14 may be disposed with shaft 80 in alternate fixation configurations, such as, for example, friction fit, pressure fit, locking protrusion/recess, locking keyway and/or adhesive.

Figure 6:
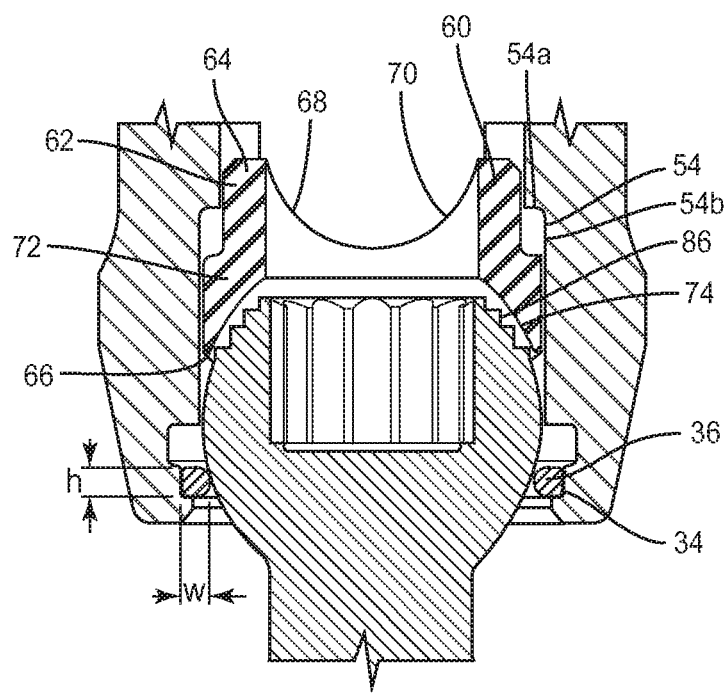
FIG. 6 is a break away, cross section view of the components shown in FIG. 1.
Figure 7:
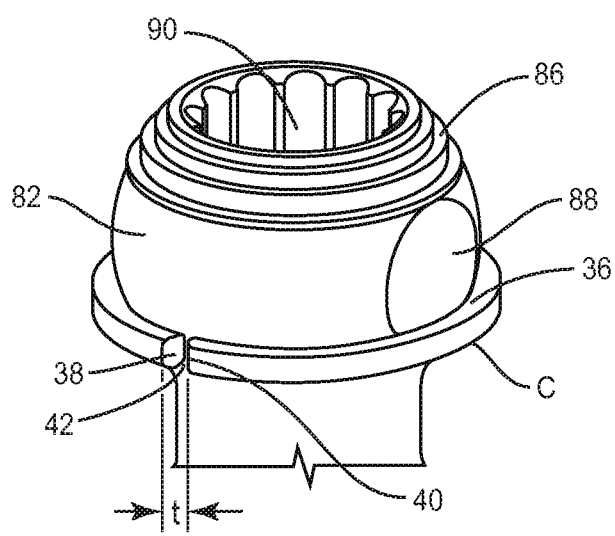
FIG. 7 is a break away view of components of the system shown in FIG. 1.

Each surface 22 defines a cavity, such as, for example, a groove 34 configured for disposal of a band, such as, for example, a C-shaped ring 36. Ring 36 includes a height h and a width w, as shown in FIG. 6. Ring 36 includes a circumference C that extends between end 38 and end 40. Ends 38, 40 define an opening, such as, for example a gap 42, as shown in FIG. 7. In some embodiments, gap 42 is sized such that gap 42 has a thickness t that is less than height h and width w. Ring 36 is configured to engage an outer surface of head 82 and is disposable with groove 34 to resist and/or prevent axial translation of shaft 80 relative to the selected receiver 14 and facilitate rotation of shaft 80 relative a selected receiver 14. In some embodiments, ring 36 is disposed within head 82 to enhance a retaining strength of bone screw 12 and resist and/or prevent shearing of shaft 80.

In some embodiments, each surface 22 includes a cavity, such as, for example, a slot 54 configured to receive a flange of a crown 60, as discussed herein. Slot 54 includes surfaces 54a, 54b. In some embodiments, all or only a portion of each surface 22 may have alternate surface configurations to enhance engagement with the spinal rod and/or the setscrew such as, for example, rough, arcuate, undulating, mesh, porous, semi-porous, dimpled and/or textured.

Crown 60 is configured for disposal within cavity 20 of the selected receiver 14. Crown 60 includes a wall 62 having an end surface 64 and an end surface 66. Surface 64 is configured to define at least a portion 68 of cavity 20. Portion 68 is defined by an outer surface 70 that defines a curved portion of crown 60 configured for engagement with a spinal rod. In some embodiments, all or only a portion of surface 70 may have alternate cross section configurations, such as, for example, oval, oblong triangular, square, polygonal, irregular, uniform, non-uniform, offset, staggered, and/or tapered.

Surface 64 defines a receiver engagement portion, such as, for example, a flange 72 configured for mating engagement with slot 54 of the selected receiver. Flange 72 includes surfaces 72a, 72b. In some embodiments, flange 72 engages the surface of slot 54 in a keyed connection such that surface 72a abuts surface 54a and surface 72b abuts surface 54b. In some embodiments, engagement of flange 72 and slot 54 prevents rotation and/or axial translation of crown 60 relative to surface 22 of the selected receiver 14. Surface 70 is disposed in fixed alignment with surface 22 for disposal of a spinal rod. Surface 66 defines an engagement portion 74 configured for engagement with head 82, as described herein.

Shaft 80 is configured to penetrate tissue, such as, for example, bone. Head 82 is interchangeably engageable with any of the plurality of receivers 14. Head 82 includes a substantially spherical proximal portion configured for moveable disposal with the selected receiver 14 and crown 60. Head 82 includes a surface 84 that defines a plurality of ridges 86 to improve purchase of head 82 with crown 60. Engagement portion 74 of crown 60 is concave or semi-spherical to accommodate the substantially spherical configuration of head 82 such that head 82 is rotatable relative to receiver 14. This configuration allows shaft 80 to be rotatable relative to axis X1 through one or a plurality of planes. In some embodiments, shaft 80 is connected to the selected receiver 14 to comprise a multi-axial fastener.

Surface 84 includes interchangeable mating surfaces, such as for example, arcuate portions 88a and planar portions, such as, for example, flats 88b that are configured for disposal with surface 30 of any of the plurality of receivers 14. Portions 88a slidable engage surface 30 and flats 88b are spaced in a non-engaging orientation with surface 30 such that surface 30 is movable relative to surface 84. Head 82 interfaces with surface 30 such that shaft 80 is rotatable along a plurality of axes, including rotation about axis X1, relative to the selected receiver 14 such that the selected receiver 14 and interchangeable shaft 80 comprise a multi-axial screw. In some embodiments, head 82 may be disposed with receiver 14 in alternate fixation configurations, such as, for example, friction fit, pressure fit, locking protrusion/recess, locking keyway and/or adhesive.

Head 82 includes a socket 90 having a hexalobe geometry configured for disposal of a similarity shaped bit of a tool, such as, for example, a driver (not shown) to engage the driver with head 82 to rotate shaft 80. Socket 90 is in communication with cavity 20 such that a driver may be inserted between arms 16, 18 and translated axially, until the bit of the driver is disposed in socket 90. In some embodiments, socket 90 has a cruciform, phillips, square, hexagonal, polygonal, star cross sectional configuration configured for disposal of a correspondingly shaped portion of a driver.

In assembly, operation and use, spinal implant system 10, similar to the systems and methods described herein, includes a selected bone screw 12, which comprises a selected receiver 14 for connection with interchangeable shaft 80 having a selected movement, and is employed with a surgical procedure for treatment of a spinal disorder affecting a section of a spine of a patient, as discussed herein. Spinal implant system 10 is employed with a surgical procedure for treatment of a condition or injury of an affected section of the spine. In some embodiments, a selected bone screw 12 comprises a selected receiver 14 for connection with a compatible shaft 80.

The components of spinal implant system 10 include a spinal implant kit, which comprises the plurality of receivers and interchangeable shafts 80. In some embodiments, spinal implant system 10 includes a spinal implant kit, which comprises the plurality of receivers and compatible shafts 80. The plurality of receivers include receivers 14 and alternate receivers, such as those described herein, that interface with interchangeable shafts 80 to comprise one or more bone screw configurations. Selected bone screws 12 and one or a plurality of spinal implants, such as, for example, vertebral rods can be delivered or implanted as a pre-assembled device or can be assembled in situ. The components of spinal implant system 10 may be may be completely or partially revised, removed or replaced.

In one embodiment, a receiver 14 is selected from the kit of the plurality of receivers 14 for interchangeable connection with shaft 80 to comprise a bone screw 12 having a selected multi-axial movement. Ring 36 is disposed with head 82, as described herein, such that circumference C extends about surface 84 of head 82 and ends 38, 40 include gap 42. Crown 60 is disposed with the selected receiver 14 such that flange 72 engages slot 54, as described herein. Surface 64 is positioned in cavity 20 to receive the spinal rod. The selected receiver 14, with crown 60 disposed therein, is engaged with head 82 causing ring 36 to engage groove 34 of the selected receiver 14. Arcuate portions 88a and flats 88b are disposed with surface 30, as described herein, such that shaft 80 is rotatable along a plurality of axes and/or within a plurality of planes of vertebrae relative to receiver 14.

In use, for treatment of a spinal disorder, shaft 80 can be threaded and engaged with tissue. In some embodiments, the selected bone screw 12 is disposed adjacent vertebrae at a surgical site and is manipulated to drive, torque, insert or otherwise connect bone screw 12 with vertebrae.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments the agent may be hydroxyapatite coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone screws 12 such as those described herein and/or fixation elements, which may be employed with a single vertebral level or a plurality of vertebral levels. In some embodiments, bone screws 12 may be engaged with vertebrae in various orientations, such as, for example, series, parallel, offset, staggered and/or alternate vertebral levels. In some embodiments, bone screws 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone screws 12 may be employed with wedges, anchors, buttons, dips, snaps, friction fittings, compressive fittings, expanding rivets, staples, nails, adhesives, posts, connectors, fixation plates and/or posts.

Figure 8:
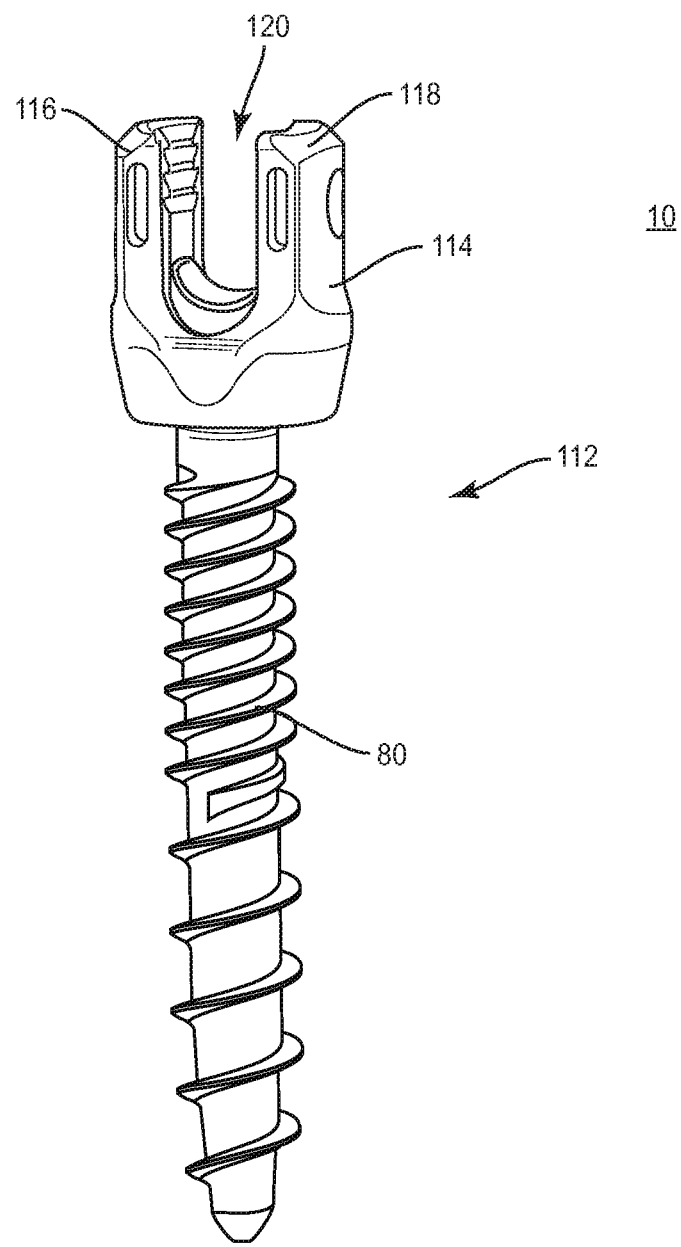
FIG. 8 is a perspective view of components of one embodiment of a spinal implant system in accordance with the principles of the present disclosure.
Figure 9:
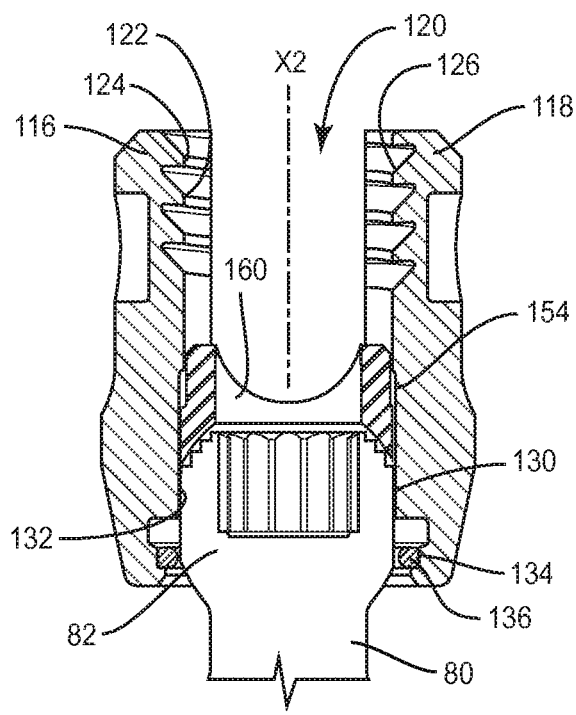
FIG. 9 is a break away, cross section view of the components shown in FIG. 8.
Figure 10:
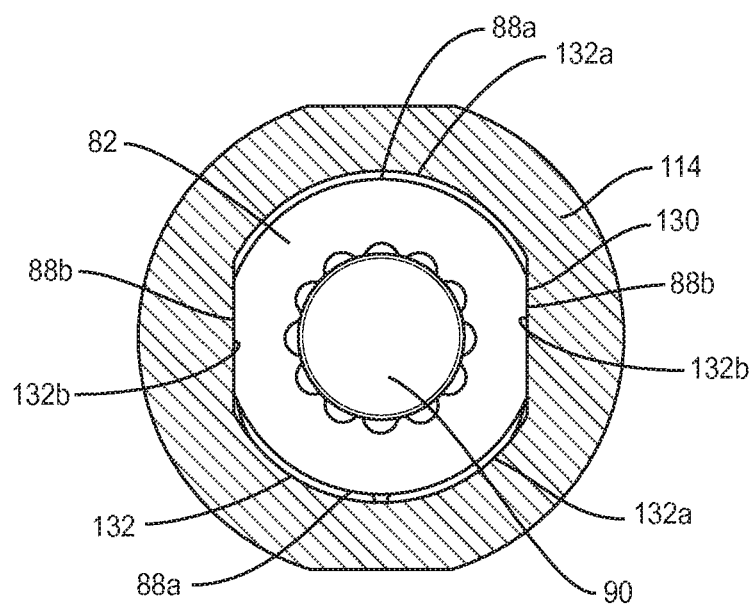
FIG. 10 is a cross section view of the components shown in FIG. 8.

In one embodiment, as shown in FIGS. 8-10, spinal implant system 10, similar to the systems and methods described herein, comprises a spinal implant kit, which includes a plurality of members, such as, for example, implant receivers 114. Receiver 114 is configured for selection from the plurality of receivers such that receiver 114 is connectable with interchangeable shaft 80, as described herein, for selected movement along a single axis and/or within a single plane to comprise a uni-axial fastener, such as, for example, a uni-axial bone screw 112. In some embodiments, spinal implant system 10 comprises a spinal implant kit, which includes receivers 114 and alternate receivers, such as those described herein. In some embodiments, spinal implant system 10 comprises a spinal implant kit, which includes receivers 14 and receivers 114. In some embodiments, receiver 114 is configured for selection from the plurality of receivers such that receiver 114 is connectable with a compatible shaft 80.

Each receiver 114 extends along an axis X2 and includes a pair of spaced apart arms 116, 118 that define an implant cavity 120 therebetween. Cavity 120 is configured for disposal of a spinal construct, such as, for example, a spinal rod (not shown). Arms 116, 118 each extend parallel to axis X2, as shown in FIG. 9. Cavity 120 is substantially U-shaped. Each receiver 114 includes an inner surface 122. A portion of surface 122 includes a thread form 124 located adjacent arm 116 and a thread form 126 located adjacent arm 118. Thread forms 124, 126 are each configured for engagement with a coupling member, such as, for example, a setscrew (now shown), to retain a spinal construct, such as, for example, a spinal rod within cavity 120.

A portion of each surface 122 defines an engagement surface 130 configured for a mating engagement with interchangeable head 82 of shaft 80 such that shaft 80 is rotatable along a single axis and/or within a single plane relative to receiver 114, such as, for example, comprising a uni-axial screw 112.

Each surface 130 of each receiver 14 includes a keyway 132 that includes mating elements, such as, for example, arcuate surfaces 132a and planar surfaces, such as, for example, flats 132b. Flats 132b are configured to interface with flats 88b of head 82 and arcuate surfaces 132a are configured to interface with arcuate surfaces 88a in a keyed connection, as shown in FIG. 10, such that shaft 80 is rotatable along a single axis and/or within a single plane relative to receiver 114. Flats 132b engage flats 88b to resist and/or prevent rotation of receiver 114 about axis X2. In some embodiments, shaft 80 is rotatable along a single axis and/or within a single plane aligned with cavity 120. In some embodiments, receiver 114 may be disposed with shaft 80 in alternate fixation configurations, such as, for example, friction fit, pressure fit, locking protrusion/recess, locking keyway and/or adhesive.

Each surface 122 defines a groove 134 configured for disposal of a C-shaped ring 136, similar to ring 36 described herein. Each surface 122 includes a slot 154 configured to receive a crown 160, similar to crown 60 described herein.

In assembly, operation and use, spinal implant system 10, similar to the systems and methods described herein, includes a selected bone screw 112, which comprises a selected receiver 114 for connection with interchangeable shaft 80 and has a selected uni-axial movement for treatment of a spinal disorder affecting a section of a spine of a patient, as discussed herein. In one embodiment, a receiver is selected from the kit of the plurality of receivers, which include receivers 114 and alternate receivers, such as those described herein, and interchangeable shafts 80. A selected receiver 114 interfaces with an interchangeable shaft 80 to comprise a bone screw 112 having a selected uni-axial movement.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   a plurality of alternate first members, each of the first members including an inner surface defining an implant cavity, the inner surfaces each defining a groove;
   a second member being configured to penetrate tissue and including a mating element engageable with one of the plurality of first members such that the second member is interchangeable with the plurality of first members, the mating element comprising flats positioned on opposite sides of the mating element;
   a circumferential ring positioned in the groove of one of the plurality of alternate first members to couple the second member to one of the plurality of alternate first members; and
   a crown disposed with the implant cavity of one of the plurality of alternate first members and engageable with the second member,
   wherein one of the plurality of first members is connected with the second member such that the flats directly engage the ring to comprise a bone fastener having a selected movement.

2. A spinal implant system as recited in claim 1, wherein the mating element interfaces with a selected one of the plurality of alternate first members such that the second member is rotatable about a plurality of axes relative to the selected first member.

3. A spinal implant system as recited in claim 1, wherein the mating element includes a head and the second member includes a shaft configured to penetrate the tissue, the shaft being rotatable about one or a plurality of axes relative to a selected one of the plurality of alternate first members.

4. A spinal implant system as recited in claim 3, wherein the head is movable relative to the inner surface of the selected first member such that the shaft pivots through a plurality of planes relative to the selected first member.

5. A spinal implant system as recited in claim 1, wherein the ring defines a gap.

6. A spinal implant system as recited in claim 5, wherein the gap defines a dimension that is less than at least one dimension of the ring.

7. A spinal implant system as recited in claim 5, wherein the gap defines a slot thickness that is less than a height and a width of the ring.

8. A spinal implant system as recited in claim 1, further comprising a spinal rod disposable with the implant cavity of one of the plurality of alternate first members.

9. A spinal implant system as recited in claim 1, wherein the mating element comprises arcuate portions between the flats.

10. A spinal implant system as recited in claim 1, wherein the crown comprises a concave bottom surface that engages the mating element.

11. A spinal implant system as recited in claim 1, wherein the plurality of alternate first members each include a first surface and a second surface that extends transverse to the first surface, the crown comprising a flange having a first surface that engages the first surface of one of the plurality of alternate first members and a second surface that engages the second surface of one of the plurality of alternate first members.

12. A spinal implant system as recited in claim 1, wherein the mating element comprises a plurality of ridges.

13. A spinal implant system as recited in claim 1, wherein the selected movement includes rotation and pivotal movement of the second member relative to one of the plurality of first members about a plurality of axes.

14. A spinal implant system as recited in claim 1, wherein the selected movement includes rotation and pivotal movement of the second member relative to one of the plurality of first members through a plurality of planes.

15. A spinal implant system as recited in claim 1, wherein the ring is configured to prevent axial translation of the second member relative to one of the plurality of alternate first members and facilitate rotation of the second member relative to one of the plurality of alternate first members.

16. A spinal implant system comprising:
a plurality of alternate implant receivers each comprising an inner surface defining a groove;
a bone screw shaft including a head engageable with a selected one of the implant receivers such that the shaft is compatible with the selected implant receiver, the head comprising flats positioned on opposite sides of the head;
a circumferential ring positioned in the groove of the selected implant receiver to couple the second member to the selected implant receiver; and
a crown disposed within an implant cavity of the selected implant receiver such that the head engages the crown, wherein the head includes an outer surface that defines a plurality of ridges to improve purchase of the head with the crown,
wherein the selected implant receiver is connected with the shaft such that the flats directly engage the ring to comprise a bone fastener having a selected movement.

17. A spinal implant system as recited in claim 16, wherein the flats are spaced apart from the inner surface of the selected implant receiver by the ring.

18. A spinal implant system as recited in claim 16, wherein an outer surface of the head includes arcuate portions that extend between the flats, the arcuate portions slidably engaging the inner surface of the selected implant receiver, the flats being spaced in a non-engaging orientation with the inner surface of the selected implant receiver such that the inner surface of the selected implant receiver is movable relative to the outer surface.

* * * * *

UNITED STATES PATENT AND TRADEMARK OFFICE
CERTIFICATE OF CORRECTION

| | |
|---|---|
| PATENT NO. | : 10,028,770 B2 |
| APPLICATION NO. | : 14/518760 |
| DATED | : July 24, 2018 |
| INVENTOR(S) | : Rezach et al. |

It is certified that error appears in the above-identified patent and that said Letters Patent is hereby corrected as shown below:

In Column 1, Line 15, delete "disc hemiation," and insert -- disc herniation, --, therefor.

In Column 7, Line 49, delete "similarity" and insert -- similarly --, therefor.

In Column 8, Line 29, delete "fiats 88b" and insert -- flats 88b --, therefor.

In Column 9, Line 3, delete "dips," and insert -- clips, --, therefor.

In Column 9, Line 48, delete "arcuate surfaces 88a" and insert -- arcuate surfaces 132a --, therefor.

Signed and Sealed this
Fourth Day of December, 2018

Andrei Iancu
*Director of the United States Patent and Trademark Office*